United States Patent
Mitchell et al.

(10) Patent No.: US 7,869,016 B2
(45) Date of Patent: Jan. 11, 2011

(54) FIBER DAMAGE DETECTION AND PROTECTION DEVICE

(75) Inventors: Gerald M. Mitchell, Los Altos, CA (US); Douglas G. Stinson, Fremont, CA (US); Michael W. Sasnett, Los Altos, CA (US); David S. Jebens, Campbell, CA (US); Michael R. Hodel, Fremont, CA (US)

(73) Assignee: AMS Research Corporation, Minnetonka, MN (US)

( * ) Notice: Subject to any disclaimer, the term of this patent is extended or adjusted under 35 U.S.C. 154(b) by 0 days.

(21) Appl. No.: 12/123,152

(22) Filed: May 19, 2008

(65) Prior Publication Data

US 2008/0285017 A1    Nov. 20, 2008

Related U.S. Application Data

(60) Provisional application No. 60/938,536, filed on May 17, 2007.

(51) Int. Cl.
| | |
|---|---|
| *G01N 21/00* | (2006.01) |
| *A61B 1/04* | (2006.01) |
| *A61B 18/18* | (2006.01) |
| *B23K 26/04* | (2006.01) |
| *B23K 26/02* | (2006.01) |

(52) U.S. Cl. .................. 356/73.1; 600/108; 606/11; 606/15; 606/16; 219/121.83; 219/121.62

(58) Field of Classification Search .................. None
See application file for complete search history.

(56) References Cited

U.S. PATENT DOCUMENTS

| | | | | |
|---|---|---|---|---|
| 3,781,092 A | * | 12/1973 | Sussman et al. ............. | 359/227 |
| 3,981,592 A | * | 9/1976 | Williams .................... | 356/73.1 |
| 4,543,477 A | * | 9/1985 | Doi et al. ................ | 250/227.11 |
| 4,589,404 A | * | 5/1986 | Barath et al. ................ | 600/108 |
| 4,682,594 A | * | 7/1987 | Mok ............................. | 606/7 |
| 4,695,697 A | * | 9/1987 | Kosa ..................... | 219/121.83 |
| 4,716,288 A | * | 12/1987 | Doi ........................ | 250/227.11 |
| 4,812,641 A | * | 3/1989 | Ortiz Jr. ....................... | 250/205 |
| 4,883,054 A | * | 11/1989 | Fuller et al. ................... | 606/12 |
| 5,012,087 A | * | 4/1991 | Rockstroh et al. ....... | 250/227.15 |
| 5,219,345 A | * | 6/1993 | Potter .......................... | 606/15 |
| 5,747,794 A | * | 5/1998 | Malchesky ............. | 250/227.23 |
| 5,772,597 A | * | 6/1998 | Goldberger et al. ......... | 600/473 |
| 7,556,414 B2 | * | 7/2009 | Hopkins et al. .............. | 362/574 |
| 2003/0216720 A1 | * | 11/2003 | Sinofsky ........................ | 606/11 |
| 2009/0062782 A1 | * | 3/2009 | Brown .......................... | 606/15 |

* cited by examiner

*Primary Examiner*—Tarifur Chowdhury
*Assistant Examiner*—Gordon J Stock, Jr.
(74) *Attorney, Agent, or Firm*—Kimberly K. Baxter; Gregory L. Koeller

(57) ABSTRACT

A medical laser system and related methods of monitoring optical fibers to determine if an optical fiber cap on the optical fiber is in imminent danger of failure. The laser system includes a photodetector for converting returned light from the optical fiber cap to an electronic signal for comparison to a trigger threshold value known to be indicative imminent fiber cap failure. The returned light can be the main laser treatment wavelength, an auxiliary wavelength such as an aiming beam or infrared wavelengths generated by a temperature of the optical fiber cap. In the event the electronic signal reaches the trigger threshold value, the laser system can be temporarily shut-off or the power output can be reduced.

10 Claims, 4 Drawing Sheets

FIBER DAMAGE DETECTION AND PROTECTION DEVICE

PRIORITY CLAIM

The present application claims priority to U.S. Provisional Application Ser. No. 60/938,536 filed May 17, 2007, and entitled "FIBER DAMAGE DETECTION AND PROTECTION DEVICE", which is hereby incorporated by reference in its entirety.

FIELD OF THE DISCLOSURE

The present invention relates generally to the field of medical lasers utilizing optical fibers. More specifically, the present invention relates to the use of a signal processing system to detect imminent optical fiber cap failure and adjust the laser to prevent optical fiber cap failure.

BACKGROUND OF THE INVENTION

Medical lasers have been used in treatment procedures involving various practice areas including, for example, urology, neurology, otorhinolaryngology, general anesthetic ophthalmology, dentistry, gastroenterology, cardiology, gynecology, and thoracic and orthopedic procedures. Generally, these procedures require precisely controlled delivery laser energy, and often the area to which the energy is to be delivered is located deep within the body, for example, at the prostate or at the fallopian tubes. Due to the location of the target tissue deep within the body, the medical procedure generally requires use of a flexible and maneuverable optical fiber. Depending upon the requirements for a light source, a variety of light sources can be used in conjunction with the optical fiber including, for example, pulsed lasers, diode lasers, and neodymium lasers. Representative lasers used in medical treatment procedures include Ho:YAG lasers and Nd:YAG lasers.

In medical procedures utilizing laser energy, the laser is coupled to an optical fiber adapted to direct laser radiation from the laser, through the fiber and to the treatment area. Typically, a surgical probe is utilized in the treatment of body tissue with laser energy. The surgical probe generally includes an optical fiber coupled to a laser source, and the probe tip or cap is positioned on the optical fiber opposite the laser source, such that the cap of the probe can be positioned adjacent the targeted tissue. Laser energy is directed out of the probe cap of the optical fiber onto desired portions of the targeted tissue. The optical fiber and surgical probe cap deliver laser radiation to the treatment area on the tissue, wherein the laser radiation has a wavelength and has an irradiance in the treatment area sufficient to cause vaporization of a substantially greater volume of tissue than a volume of residual coagulated tissue caused by the laser radiation.

An optical fiber generally consists of a core surrounded by cladding, which in turn is surrounded by a buffer and a jacket. The cladding has a lower refractive index than the core does, and light travels along the fiber as a result of the difference in the indices of refraction of the core and cladding materials. Light is kept in the core of the optical fiber by internal reflection of light, thus causing the fiber to act as a waveguide. The jacket of the fiber is designed to protect the optical fiber during use and storage, and is generally made of a thin layer of material including, for example, metal, plastic, polyimide, nylon, or fluoropolymer.

The laser system can fail due to the failure of the optical fiber. In particular, the failure of a cap on a treatment of the optical fiber can cause the laser system to fail. Failure of the cap can require replacement of the optical fiber cap or the entire optical fiber. Failure of the cap is especially critical if it occurs during treatment and pieces of the failed optical fiber must be flushed out or picked out of the patient and a new optical fiber must be installed. Further, failure of the cap can complicate performance of the procedure, delay performance of the scheduled medical procedure, and raise operating costs due to delay and the need for replacement parts. Hence, there remains a need for preventing failure of the laser system and, in particular, of the optical fiber.

SUMMARY OF THE INVENTION

The present invention comprises a medical laser system and related methods of monitoring optical fibers to determine if an optical fiber cap on the optical fiber is in imminent danger of failure. The laser system includes a photodetector for converting returned light from the optical fiber cap to an electronic signal for comparison to a trigger threshold value known to be indicative imminent fiber cap failure. The returned light can be the main laser treatment wavelength, an auxiliary wavelength such as an aiming beam or infrared wavelengths generated by a temperature of the optical fiber cap. In the event the electronic signal reaches the trigger threshold value, the laser system can be temporarily shut-off or the power output can be reduced. Should the trigger threshold be reached during a medical procedure, the laser unit can be adjusted such that the medical procedure can be continued without interruption. For example, the light output power of the laser can be reduced to prevent optical fiber cap failure.

In another aspect, the present invention is directed to a method for determining imminent failure of a fiber cap on an optical fiber used for medical laser treatment. Generally, the method comprises providing an optical fiber having a distal end with an attached fiber cap and a proximal end attached to a medical laser unit. With the optical fiber attached as such, light returning from the distal end can be captured at the proximal end. The returned light can comprise a main laser treatment wavelength, an auxiliary wavelength such as, for example, an aiming beam or an infrared wavelength indicative of a temperature of the fiber cap. The captured light can be converted to an electronic signal with a photodetector. The electronic signal can then be compared to a trigger threshold value known to be associated with imminent failure of the fiber cap. Upon the electronic signal reaching the trigger threshold value, the medical laser unit can be shut off or alternatively, have its power reduced to extent the life of the fiber cap. In some embodiments, the method can further comprise filtering the returned light to remove wavelength noise prior to converting the captured light to the electronic signal. In yet other embodiments, the method can further comprise sounding an audible alarm to indicate to a medical professional when the trigger threshold value has been reached.

The above summary of the various representative embodiments of the invention is not intended to describe each illustrated embodiment or every implementation of the invention. Rather, the embodiments are chosen and described so that others skilled in the art may appreciate and understand the principles and practices of the invention. The figures in the detailed description that follows more particularly exemplify these embodiments.

BRIEF DESCRIPTION OF THE DRAWINGS

These as well as other objects and advantages of this invention, will be more completely understood and appreciated by referring to the following more detailed description of the presently preferred exemplary embodiments of the invention in conjunction with the accompanying drawings of which.

Figure 1:
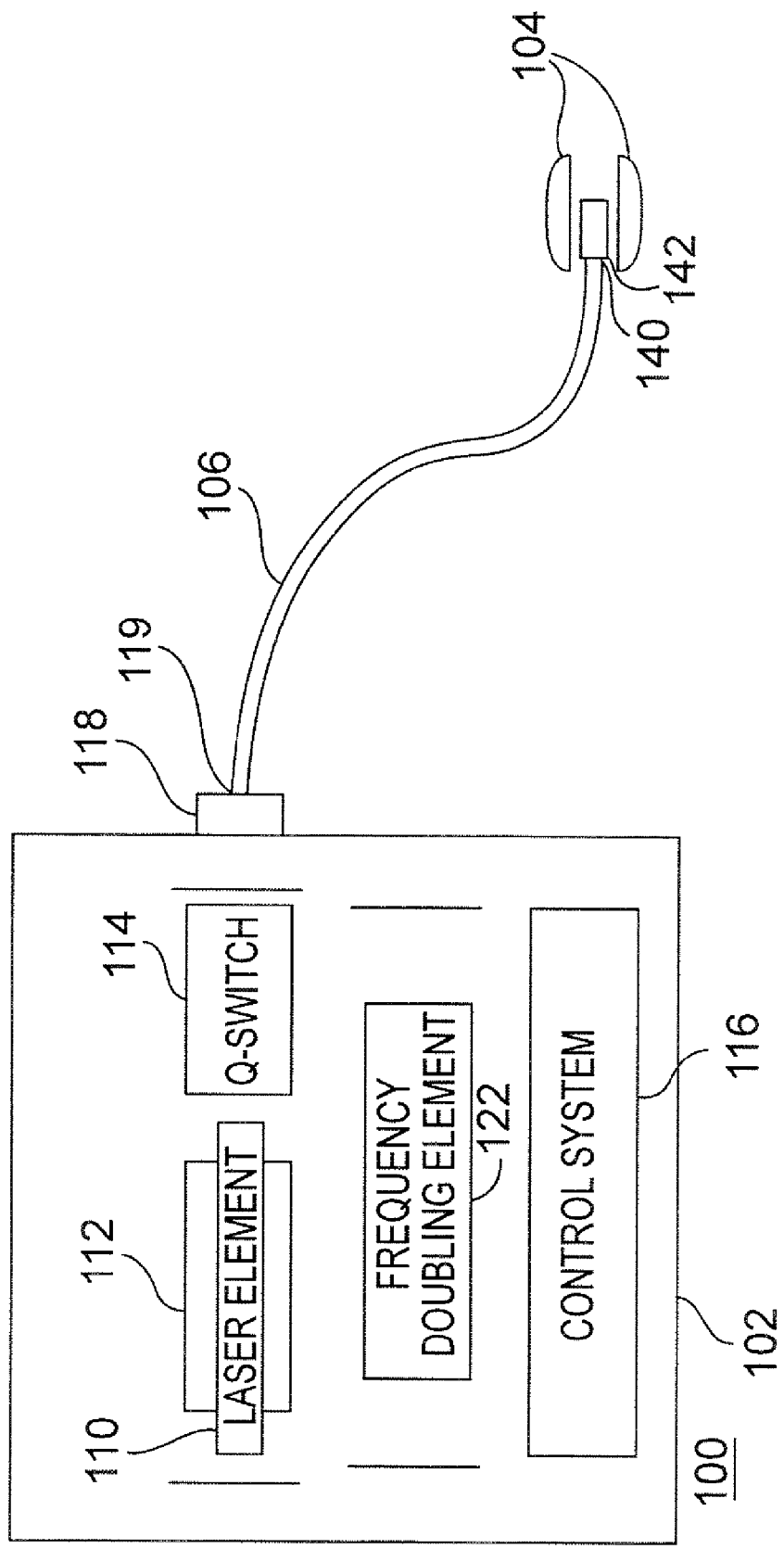
FIG. 1 is a block diagram illustration of a laser system according to an embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives.

DETAILED DESCRIPTION OF EMBODIMENTS OF THE INVENTION

The present invention comprises a medical laser system and related methods of monitoring an optical fibers to determine if an optical fiber cap on the optical fiber is in imminent danger of cap failure. The laser system includes a photodetector for converting returned light from the optical fiber cap to an electronic signal for comparison to a trigger threshold value known to be indicative imminent fiber cap failure. The returned light can be the main laser treatment wavelength, an auxiliary wavelength such as an aiming beam or infrared wavelengths generated by a temperature of the optical fiber cap. In the event the electronic signal reaches the trigger threshold value, the laser system can be temporarily shut-off or the power output can be reduced. In one preferred embodiment, the present invention can be utilized as part of a Greenlight HPS system manufactured by American Medical Systems of Minnetonka, MN and as described in U.S. Pat. Nos. 6,554,824 and 6,986,764, which are herein incorporated by reference.

Referring to FIG. 1, there is depicted a block diagram showing an exemplary laser system 100 which may be employed for implementing the present invention. Laser system 100 includes a solid-state laser unit 102, which is used to generate laser light for delivery through optical fiber 106 to target tissue 104. Laser unit 102 is capable of being operated in a pulsed mode or continuous wave.

Laser unit 102 more specifically comprises a laser element assembly 110, pump source 112, and frequency doubling crystal 122. In the preferred-embodiment, laser element 110 outputs 1064 nm light which is focused into frequency doubling crystal 122 to create 532 nm light. According to one implementation, laser element assembly 110 may be neodymium doped YAG (Nd:YAG) crystal, which emits light having a wavelength of 1064 nm (infrared light) when excited by pump source 112. Laser element 110 may alternatively be fabricated from any suitable material wherein transition and lanthanide metal ions are disposed within a crystalline host (such as YAG, Lithium Yttrium Fluoride, Sapphire, Alexandrite, Spinel, Yttrium Orthoaluminate, Potassium Gadolinium Tungstate, Yttrium Orthovandate, or Lanthahum Scandium Borate). Laser element 110 is positioned proximal to pump source 112 and may be arranged in parallel relation therewith, although other geometries and configurations may be employed.

Pump source 112 may be any device or apparatus operable to excite laser element assembly 110. Non-limiting examples of devices which may be used as pump source 112, include: arc lamps, flashlamps, and laser diodes.

A Q-switch 114 disposed within laser unit 102 may be operated in a repetitive mode to cause a train of micropulses to be generated by laser unit 102. Typically the micropulses are less than 1 microsecond in duration separated by about 40 microseconds, creating a quasi-continuous wave train. Q-switch 114 is preferably of the acousto-optic type, but may alternatively comprise a mechanical device such as a rotating prism or aperture, an electro-optical device, or a saturable absorber.

Laser unit 102 is provided with a control system 116 for controlling and operating laser unit 102. Control system 116 will typically include a control processor which receives input from user controls (including but not limited to a beam on/off control, a beam power control, and a pulse duration control) and processes the input to accordingly generate output signals for adjusting characteristics of the output beam to match the user inputted values or conditions. With respect to pulse duration adjustment, control system 116 applies an output signal to a power supply (not shown) driving pump source 112 which modulates the energy supplied thereto, in turn controlling the pulse duration of the output beam.

Although FIG. 1 shows an internal frequency doubled laser, it is only by way of example. The infrared light can be internally or externally frequency doubled using non-linear crystals such as KTP, Lithium Triborate (LBO), or Beta Barium Borate (BBO) to produce 532 nm light. The frequency doubled, shorter wavelength light is better absorbed by the hemoglobin and char tissue, and promotes more efficient tissue ablation. Finally, the green light leaves only a thin char layer with little pre and post operative bleeding.

Laser unit 102 further includes an output port 118 couplable to a proximal end 119 of optical fiber 106. Output port 118 directs the light generated by laser unit 102 into optical fiber 106 for delivery to tissue 104. While a bare fiber may be utilized for certain procedures, optical fiber 106 preferably terminates in a distal tip 140 having a fiber cap 142 for shaping and/or orienting the beam emitted by optical fiber 106 so as to optimize the tissue ablation process, for example a side-firing fiber.

In order to accomplish a successful medical procedure, it is important that the optical fiber 106 perform properly. Of the various possible failure modes during use of laser system 100, a primary failure mode in laser system 100 is failure of fiber cap 142. Shortly before failure of the fiber cap 142, light returning through the optical fiber 106 changes in intensity. To prevent failure of the fiber cap 142, light returning through the optical fiber 106 can be measured so as to determine when the laser light intensity begins to change.

Figure 2:
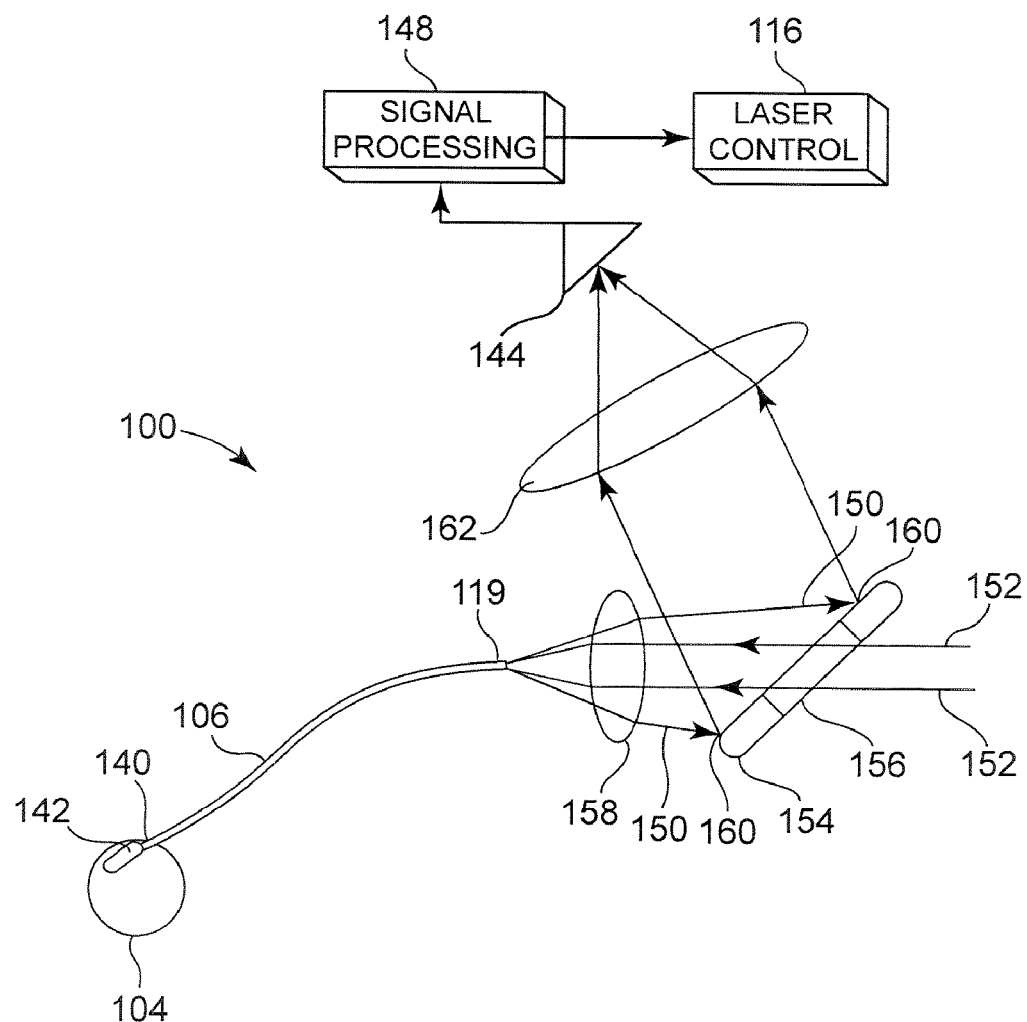
FIG. 2 is a schematic diagram of the laser system of FIG. 1.

To measure the intensity of the returning laser light, a portion of the laser light can be directed to a photodetector or photodiode 144 for conversion into an electrical signal as shown in FIG. 2. The photodetector or photodiode 144 used is dependent, at least in part, on the wavelength that is to be measured. The photodetector or photodiode 144 is designed to detect abnormal wavelengths radiating from proximal end 119 of the optical fiber 106, at which time failure of the fiber cap 142 can be imminent. A signal processor is used to compare and identify characteristics of the electrical signal that are highly correlated to failure of the fiber cap 142. If the electrical signal includes characteristics that are highly correlated to imminent failure of fiber cap 142, control system 116 can be adjusted to reduce the laser power until the electrical signal is characteristic of normal operation or turn off the laser unit 102 completely.

Returned laser light 150 through the optical fiber 106 can be more divergent than incident laser light 152 on the optical fiber 106 from the laser unit 102. A mirror 154 containing an aperture 156 in the center of the mirror 154 is placed so that the incident laser light 152 passes undisturbed through the mirror 154. A coupling lens 158 is placed between the mirror 154 and the proximal end 119 of the optical fiber 106. The incident laser light 152 passes through the aperture 156 in the mirror 154 and is launched into the optical fiber 106 by the coupling lens 158. The laser unit 102 continues to operate normally. The returned laser light 150 impinges on an outer annulus 160 of the mirror 154 and is directed by use of light manipulating means on to the photodetector 144. The light manipulating means can include a focusing lens 162 or the like. The photodetector 144 can include a transimpedance amplifier, a voltage gain stage and a current buffer.

Figure 3:
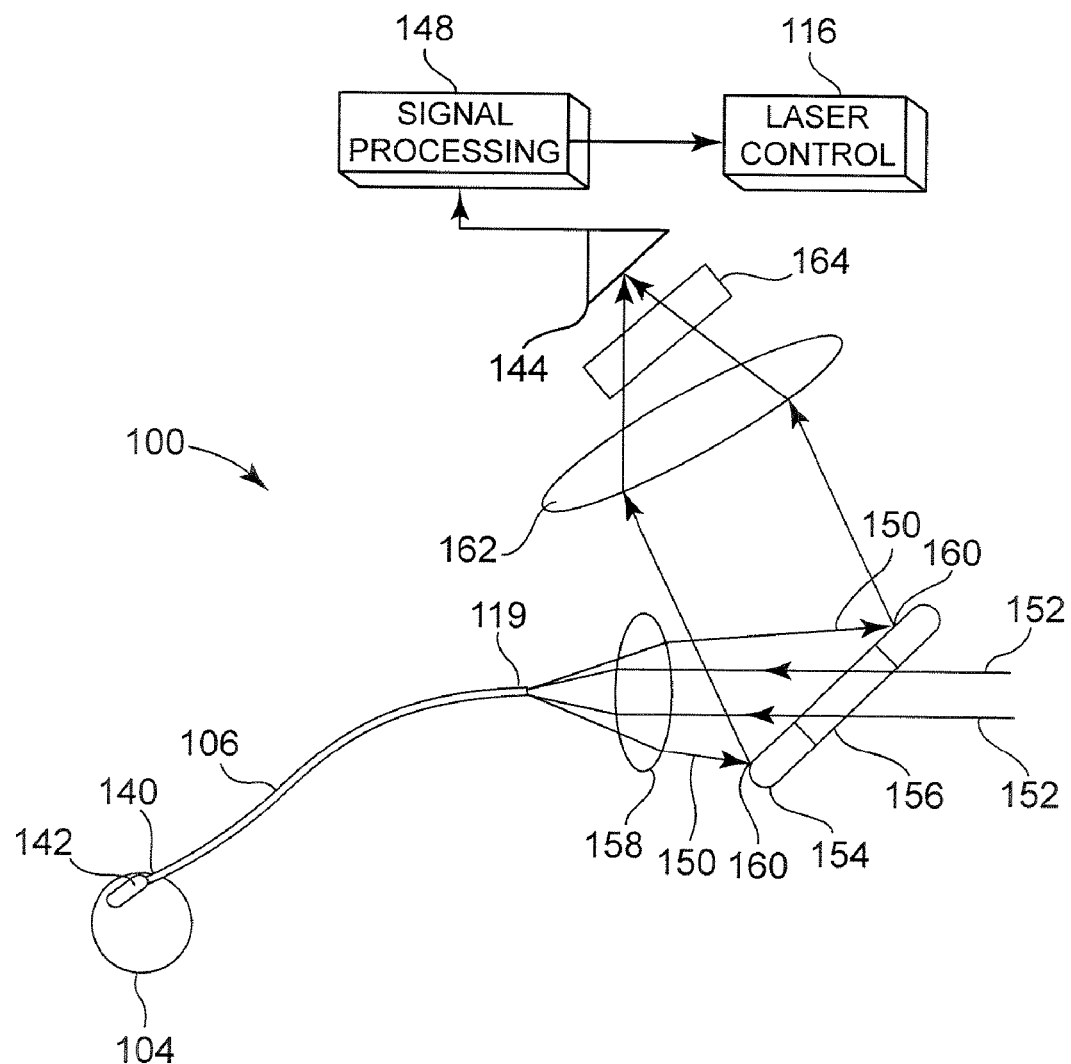
FIG. 3 is a schematic diagram of a laser system according to an embodiment of the present invention.

In an alternative embodiment as illustrated in FIG. 3, optical filters 164 can be added to the apparatus to block-out particular wavelengths. Optical filters 164 can be placed between the focusing lens 162 and the photodetector 144. The optical filters 164 operate to eliminate background light at wavelengths which are not of interest to the determination of potential or imminent failure of the fiber cap 142. The optical filters 164 improve the signal to noise ratio and facilitate detection of the electronic signal characteristic of imminent failure of the fiber cap 142.

In either of the above described embodiments, a portion of the laser light is directed to the photodetector 144 and converted into an electrical signal. The output signal from the photodetector 144 and a related signal conditioning board is fed to the signal processor 148 such as, for example, an analog/digital converter. As noted above, the electronic signal is processed and software can be used to set a trigger threshold value at which point, power from laser unit 102 can in some instances be reduced or even shut-off by the control system 116 to protect the fiber cap 142. The trigger threshold value generally comprises a predetermined value, which has previously been determined to be highly indicated of imminent failure of the fiber cap 142. In addition, the trigger threshold value can trigger sounding of an audible alarm to warn a medical professional that an imminent problem is developing with the fiber cap 142. In the event of a temporary shut-off of laser unit 102, fiber cap 142 is protected until conditions at the fiber cap 142 normalize such that normal operation of laser unit 102 can be resumed.

The returned laser light 150 that is used to detect the signal indicative of the status of the fiber cap 142 can be the main treatment wavelength of the laser unit; for example, a 532 nm beam. Alternatively, an auxiliary wavelength can be used. One representative auxiliary wavelength can comprise an aiming wavelength such as, for example, an aiming wavelength operating at 635 nm. Use of the auxiliary wavelength to detect the signal indicative of imminent failure of fiber cap 142 allows for continued monitoring of the signal formed from the auxiliary wavelength while the control system directs the main treatment wavelength to be shut off.

An alternative to monitoring returned laser light 150 is to monitor and detect infrared light transmitted back through the optical fiber 106. Infrared light transmitted back through the optical fiber 106 provides an indication of a temperature of the fiber cap 142. The infrared radiation is generated by the heat of fiber cap 142. When the temperature of fiber cap 142 exceeds a preset critical value, an audible alarm sounds and the laser unit 102 is turned off or is turned down in power. Alternatively, or in addition, a signal can be provided to the medical professional when the temperature of the fiber cap 142 reaches a critical value such that the medical professional can make the necessary adjustments to the laser system 100.

Infrared light in the range of 1450 nm to 1800 nm is the most useful range of light for detecting impending damage of the fiber cap 142, as it is a sensitive measure of temperature in the most critical area of the fiber cap 142. Infrared light generated at a distal end of the fiber cap 142 radiates back through the coupling lens 158, to the mirror 154, and on to the photodetector 144. The photodetector 144 can comprise an IndiumGalliumArsenide photodiode alternatively, a germanium detector can be used. In a preferred embodiment, IndiumGalliumArsenide photodetector 144 is optimally suited for wavelengths larger than 1450 nm. The photodetector 144 is designed to detect blackbody radiation radiating from the fiber cap 142 under abnormal conditions which can lead to elevation of the fiber cap 142 to a destructive temperature. In some embodiments, optical filters 164 can be placed between the focusing lens 162 and the photodetector 144. For example, optical filter 164 can be a spectral filter that blocks out wavelengths shorter than 1450 nm. Alternatively or in addition, optical filter 164 can include a spatial filter consisting of a beam tube with a non-reflective coating to prevent long wavelength noise from saturating the photodetector 144. The output signal from photodetector 144 is transmitted to the signal processor, which determines if the signal is indicative of imminent failure of the fiber cap 142e. Accordingly, if damage to the fiber cap 142 is imminent, an audible alarm can be sounded, and the laser unit shut-off until the detected signal drops below a given threshold value. Reflected light and infrared light transmitted back through optical fiber 106 can both be monitored and detected.

Figure 4:
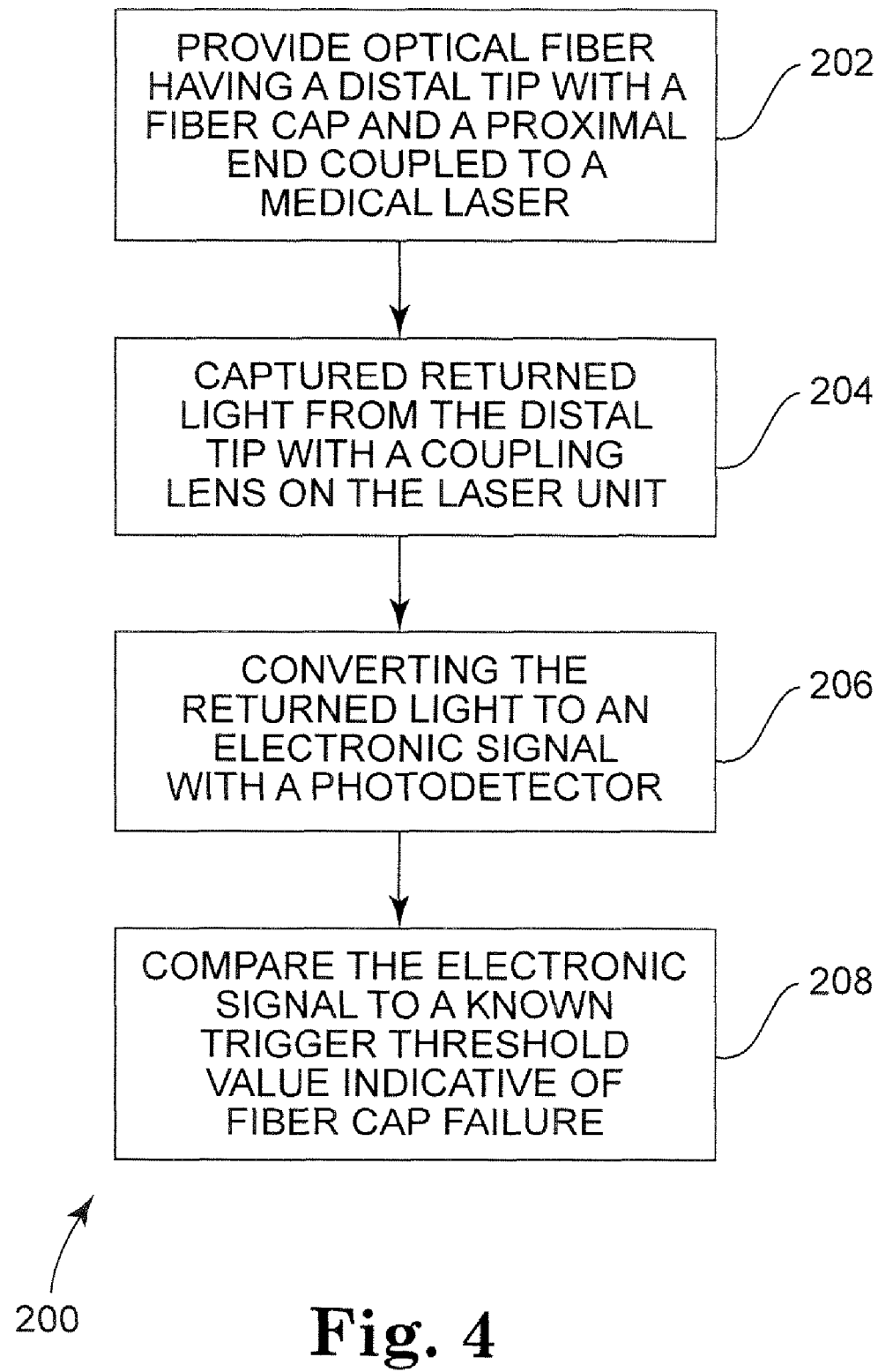
FIG. 4 is a flow chart illustrating a method of determining imminent failure of a fiber cap on an optical fiber used for medical laser treatment according to an embodiment of the present invention.

Referring now to FIG. 4, a method 200 is illustrated for detecting imminent failure of fiber cap 142 on optical fiber 106 used with laser unit 102. The method generally comprises a first step 202 of providing optical fiber 106 with a distal tip 140 having an attached fiber cap 142 and a proximal end 119 attached to the laser unit 102 at output port 118. In a second step 204, returned light from the distal tip 140 is captured by coupling lens 158. As discussed above, the returned light can comprise the main laser treatment wavelength, an auxiliary wavelength such as, for example, an aiming beam or an infrared wavelength indicative of a temperature of the fiber cap 142. In a third step 206, the returned light is directed to photodetector 144 where the returned light is converted to an electronic signal. In a fourth step 208, the electronic signal is compared to a known trigger threshold value associated with imminent failure of the fiber cap 142. Method 200 can comprise additional steps such as, for example, filtering the returned light with optical filter 164 to remove wavelength noise prior to third step 206. Method 200 can further comprise powering down or shutting off the laser unit 102 upon the electronic signal reaching the trigger threshold value. Method 200 can further comprise providing an audible signal to a medical professional indicating when the electronic signal reaches the trigger threshold value.

The ability to detect imminent failure of the fiber cap 142 allows for action to be taken by a medical professional to prevent damage to the fiber cap 142. By taking action to prevent damage to the fiber cap 142, fewer optical fibers 106 are damages and therefore, fewer medical laser procedures are interrupted and these procedures are conducted with greater safety.

Although specific examples have been illustrated and described herein, it will be appreciated by those of ordinary skill in the art that any arrangement calculated to achieve the same purpose could be substituted for the specific examples shown. This application is intended to cove adaptations or variations of the present subject matter. Therefore, it is intended that the invention be defined by the attached claims and their legal equivalents.

We claim:

1. A method for determining imminent failure of a fiber cap on an optical fiber used for medical laser treatment comprising:
   providing an optical fiber having a distal tip with an attached fiber cap and a proximal end coupled to a medical laser unit;
   capturing light returning from the fiber cap at the proximal end of the optical fiber, wherein capturing light returning from the fiber cap at the proximal end comprises capturing an auxiliary wavelength of the medical laser unit;
   filtering the returned light to isolate the captured auxiliary wavelength;
   converting the captured auxiliary wavelength to an electronic signal;
   comparing the electronic signal to a trigger threshold value associated with imminent failure of the fiber cap; and
   adjusting an output of a main treatment wavelength of the medical laser unit upon the electronic signal meeting or exceeding the trigger threshold value prior to actual failure of the fiber cap to prolong the life of the fiber cap.

2. The method of claim 1, further comprising:
   shutting off the medical laser unit upon reaching the trigger threshold value.

3. The method of claim 1, further comprising:
   sounding an audible alarm upon reaching the trigger threshold value.

4. The method of claim 1, further comprising:
   reducing a laser output of the medical laser unit upon reaching the trigger threshold value.

5. The method of claim 1, further comprising:
   filtering the returned light to remove wavelength noise prior to signal conversion.

6. A medical laser system capable of detecting imminent fiber cap failure, comprising:
   a medical laser unit operably coupled to a proximal end of an optical fiber and adapted to output a main treatment wavelength through the optical fiber, the optical fiber including a fiber cap mounted at a distal tip of the optical fiber;
   a coupling lens, wherein said coupling lens captures returned light from the distal tip, wherein the returned light comprises an auxiliary wavelength of the medical laser unit;
   at least one optical filter, wherein said optical filter filters the returned light to isolate the captured auxiliary wavelength;
   a photodetector, wherein said photodetector converts the captured auxiliary wavelength light returning from the distal tip to an electronic signal; and
   a signal processor, wherein said signal processor compares the electronic signal to a trigger threshold identified with imminent failure of the fiber cap, wherein upon the electronic signal meeting or exceeding the trigger threshold adjusting the output of the main treatment wavelength of the medical laser unit prior to actual failure of the fiber cap to prolong the life of the fiber cap.

7. The medical laser system of claim 6, wherein the auxiliary wavelength comprises an aiming beam of the medical laser unit.

8. The medical laser system of claim 6, further comprising:
   a mirror having an aperture wherein light incident on the mirror passes undisturbed to the coupling lens and the returned light is passed to a focusing lens.

9. The medical laser system of claim 8, wherein the focusing lens directs the returned light to the photodetector.

10. The medical laser system of claim 9, wherein said optical filter is inline between the focusing lens and the photodetector and adapted to remove wavelength noise in the returned light prior to converting the returned light to the electronic signal with the photodetector.

* * * * *